United States Patent [19]
Sarkozi

[11] Patent Number: 4,958,631
[45] Date of Patent: Sep. 25, 1990

[54] SELF ADJUSTING, SOFT NECK SUPPORT COLLAR

[76] Inventor: Jeff Sarkozi, 1117 N. Avila Pl., Orange, Calif. 92669

[21] Appl. No.: 415,872

[22] Filed: Oct. 2, 1989

[51] Int. Cl.$^5$ .................................................. A61F 5/00
[52] U.S. Cl. .................................................. 128/87 B
[58] Field of Search ............... 128/DIG. 23, 87 B, 75; 2/415

[56] References Cited

U.S. PATENT DOCUMENTS

| | | | |
|---|---|---|---|
| 3,916,885 | 11/1975 | Gaylord, Jr. | 128/87 B |
| 3,964,474 | 6/1976 | Fox | 128/DIG. 23 |
| 4,502,471 | 3/1985 | Owens | 128/87 B |
| 4,562,833 | 1/1986 | Pujals, Jr. | 128/87 B |
| 4,582,051 | 4/1986 | Greene et al. | 128/87 B |
| 4,700,697 | 10/1987 | Mundell et al. | 128/87 B |
| 4,708,129 | 11/1987 | Pujals, Jr. | 128/87 B |

OTHER PUBLICATIONS

Hugh Smythe-The "Repetitive Strain Injury Syndrome" is Referred Pain from the Neck; Nov. 15, 1988; The Journal of Rheumatology, pp. 1604–1608.
Disorders of the Cervical Spine; Chapter 12, pp. 236–278; John H. Bland; 1987-W. B. Sauders Company.
Johnson, et al.-Cervical Orthoses; Apr., 1977; The Journal of Bone and Joint Surgery, vol. 59-A, No. 3; pp. 332–339.
Hartman, et al; Cineradiography of the Braced Normal Cervical Spine; No. 109, Jun., 1975; Clinical Orthopedics and Related Research; pp. 97–102.

Primary Examiner—Richard J. Apley
Assistant Examiner—Glenn Richman
Attorney, Agent, or Firm—Willie Krawitz

[57] ABSTRACT

A soft neck support collar is disclosed comprising two offset and attached, tubular ring elements, each element hooking together at their respective ends. Both ring elements contain a soft fill material such as nylon, cotton, polyester, arcylics, foam chips, etc. The combined effect of the fill material together, with the tubular configuration, enables the neck to adjust for lateral, forward and backward forces during movement. The upper ring element is tapered at each end, so that when these ends are joined together, a space is formed into which the chain can fit, thereby maintaining the neck in a neutral position, and preventing hyperextension.

The lower ring element is hooked together at each end, and the rings are offset to enable the lower ring to close at the back of the neck, approximately opposite from the closure of the upper ring element. Hence, the lower ring element functions as a continuous, uniform, tubular-shaped ring which does not interfere with movement of the chin. Thus, in the closed configuration, the neck support collar allows for netural positioning of the chin and neck, and restricts neck mobility.

6 Claims, 1 Drawing Sheet

SELF ADJUSTING, SOFT NECK SUPPORT COLLAR

BACKGROUND OF THE INVENTION:

This invention relates to a new and improved self adjustable, soft neck support collar which adjusts for and restrains lateral, forward and backward movement of the neck to ensure neutral positioning of the chin and neck.

A wide variety of neck support collars are in the market, and typical collars are disclosed in U.S. Pat. Nos. 1,964,962; 2,389,690; 2,806,471; 3,964,474; 4,582,051; 4,700,697; and, 4,708,129. Some of these patents describe devices which are air inflatable, and while these devices provide support for a user's neck, this support obviously will not be adjustable, since air is the supporting medium. Other of these patented devices describe fairly complicated collars which are expensive, and still other of these patents describe devices which require adjustable straps. Still other patents describe soft, solid foam neck support collars, but these support collars fail to provide sufficient resiliency when the neck is at rest, and they provide insufficient resistance to lateral, forward or backward and bending of the neck. Furthermore, solid foam materials in general tend to buckle about midway along their length due to applied pressure caused by neck motion.

It would be desirable to provide a soft neck support device which has a simple construction, and is inexpensive to manufacture. Also, the device should impart suitable neck restraint, and is self adjusting in the sense that as the user's neck moves from away from an erect position, the neck support provides increasing resistance in the direction of neck motion, rather than buckling.

THE INVENTION

According to the invention, there is provided an adjustable neck support comprising two attached, superposed tubular elements connected at their respective ends, each element containing a soft fill material, and both elements being sized and shaped to fit around a user's neck.

The upper tubular element is tapered at each end, so that upon closure it defines an open shape which fits into the user's chin. The lower tubular element is offset to the upper element, so that when the ends of the lower tubular element are connected, they will close at the rear of the neck, without interfering with the operation of the upper tubular element. Generally, the lower tubular element is closed at the back of the user's neck.

The soft fill material employed in the tubular elements is typically cotton, polyester, nylon, acrylic polymers, chip foam, etc. These materials, unlike solid foam, provide a neck support which permits the user's neck to be comfortably supported, and which will readily adjust to the weight and configuration of the chin and neck, when at rest. When the neck and chin deviate from an erect position, they will cause the neck support to become deformed, without buckling, and also provide a progressively increasing support as the neck and chin increasingly deviate from the erect position, until little or no further movement occurs.

DESCRIPTION OF THE PREFERRED EMBODIMENTS

Figure 1:
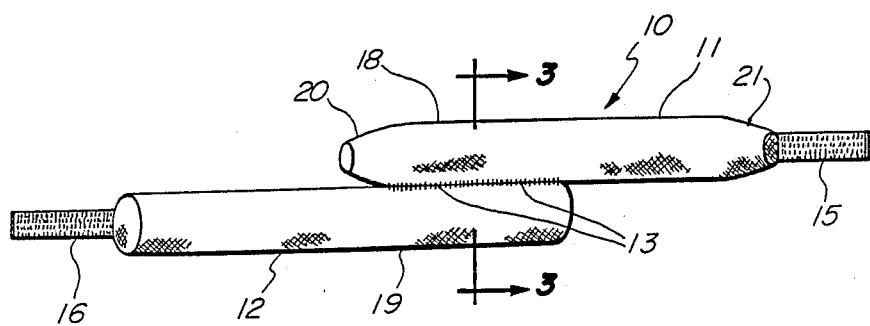
FIG. 1 is an external view in side elevation, showing the adjustable neck support of this invention.
Figure 2:
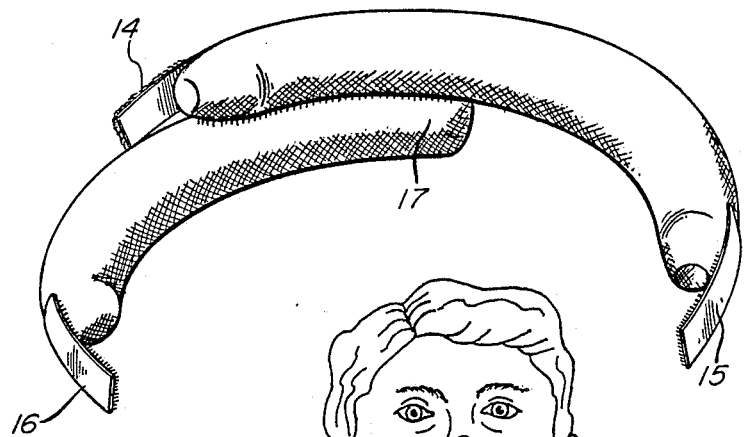
FIG. 2 is an external, upper perspective view of the neck support.

The adjustable neck support 10 of this invention is shown in FIGS. 1 and 2, and comprises upper and lower tubular elements 11 and 12, offset with respect to each other, and joined by a plurality of stitchings 13 entirely along the overlapping areas of the tubular elements; this secures the tubular elements together against relative motion. In use, the respective ends of the tubular elements 11 and 12 are joined together by fasteners 14, 15 and 16, 17 which may be constructed of VELCRO, hook elements, laces, etc.

Figure 3:
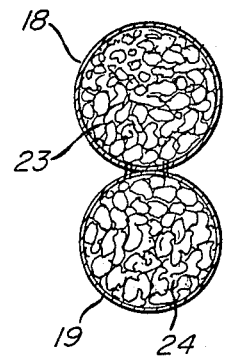
FIG. 3 is a cross sectional view of the neck support, taken along lines 3—3 of FIG. 1.

The covering materials 18, 19 of the respective tubular elements 11 and 12 are preferably constructed of woven cloth such as cotton, polyester, nylon, acrylic polymers, and blends of these, etc. As shown in FIG. 3, the interiors 23, 24 of the tubular elements contain a soft fill, such as cotton, polyester, nylon, acrylic polymers, fiber fill, loose gauze, down, chip foam, etc., and mixtures of these.

Figure 4:
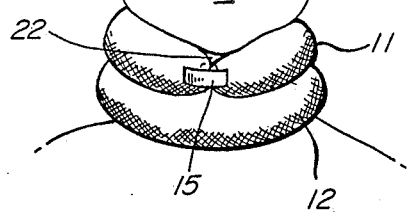
FIG. 4 is a front elevation view showing the neck support installed around a user's neck.

As shown in FIGS. 1 and 2, each end of the upper tubular element 11 is tapered 20, 21 so that upon closure, a chin support 22 is formed where the ends meet. Thus, when the neck support 10 is installed, as shown in FIG. 4, the chin of the user fits into, and is supported in an appropriate position by the chin support. Also, when the tubular element 12 is closed at the back of the user's neck, it will then form a continuous ring. Hence, the user's chin is supported and fixed in position by the chin support, as indicated, and the chin support in turn is supported by the lower tubular element 12. The soft fill of the interiors 23, 24 of the tubular elements in this configuration is sufficiently flexible to self adjust for different shapes, sizes and weights of the user's neck and chin regions.

Figures 5, 6:
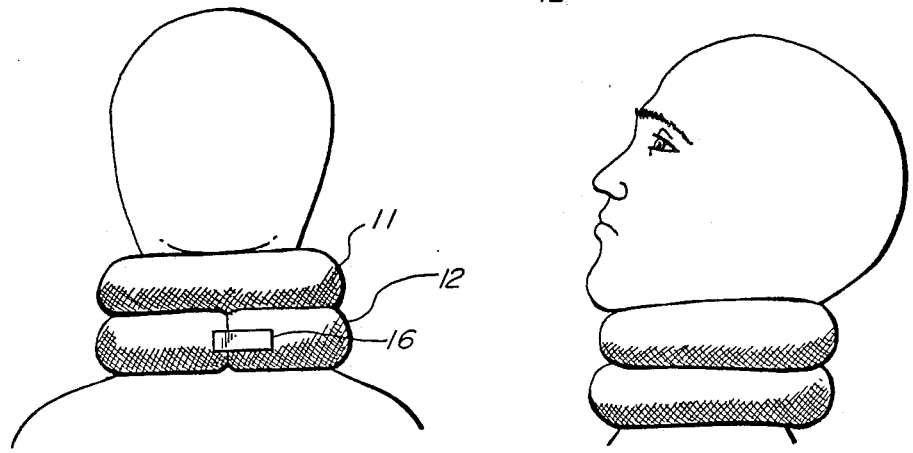
FIG. 5 is a rear elevation view of the installed neck support.
FIG. 6 is a side elevation view of the installed neck support.

FIGS. 4 and 5 illustrate the device when installed, and typically, as shown in these two Figures, the neck support 10 will maintain the neck aligned in the erect position.

As indicated, one of the unique features of this invention is the capability of maintaining a resilient support which increases as the user's neck and chin deviate from the erect position.

Additionally, another unique feature of this invention enables the extent of resilience to be varied by employing a particular fill material, or by varying the size and packing density of the fill, or by adjusting the diameter of the tubular elements, or by any combination thereof.

The tubular elements 11 and 12 vary in size from about 1"–4" in diameter, and have different lengths, depending on user neck sizes. Furthermore, their simple design makes them easy and inexpensive to manufacture. Also, the orientation of the tubular components with respect to each other permits them to self adjust to the user at rest, as well as during movement of the neck and chin without undue discomfort, considering the typical nature of the user's medical problem.

I claim:

1. A self adjusting, soft, neck support collar, comprising:
   (a) an upper, tubular-shaped element providing an outer, woven cloth covering material and an interior which contains a soft fill material, the tubular-shaped element defining tapered ends which are adapted for closure under a user's chin by closure elements mounted at each end, to thereby form a ring which fits upwardly around a user's neck; and,
   (b) a lower, tubular-shaped element providing an outer, woven cloth covering material, and shaped to form an interior which contains a soft fill material, the lower tubular-shaped element being adapted for closure at each end by closure elements to form a ring which fits around the lower portion of the user's neck, the upper tubular element resting on and being joined to the lower tubular element along a portion of their lengths so that the closure portions of each tubular element are offset from each other, the closure portion of the lower tubular element being positioned rearwardly on the neck of the user; whereby,
   i. the tapered closure portion of the upper element and adjacent lower, tubular element define a chin support for the user; and,
   ii. the soft fill materials of the upper and lower tubular elements interiors function to: 1. impart a flexible support for the user's neck and chin which self adjusts for different shapes, sizes and weights of the user's neck and chin regions; 2. maintain a resilient support which increases as the user's neck and chin deviate from an erect position, during motion; and, 3. self adjust to the user in a rest position.

2. The neck support collar of claim 1, in which the outer woven covering of the tubular neck support elements is selected from the class consisting of cotton, nylon, polyester, acrylics, and blends thereof.

3. The neck support collar of claim 2, in which the soft fill interiors of the tubular neck elements are selected from the class consisting of cotton, polyester, nylon, acrylic polymers, fiber fill, loose gauze, chip foam, down, and mixtures thereof.

4. The neck support collar of claim 1, in which the lower tubular ring functions as a continuous, uniform, tubular-shaped ring upon closure.

5. The neck support collar of claim 4, in which the lower tubular ring closes at the back of the user's neck approximately opposite from the closure of the upper, tubular ring.

6. The neck support of claim 1, in which the upper, and lower tubular rings are joined together by sewing.

* * * * *